(12) United States Patent
Swartz et al.

(10) Patent No.: US 11,439,316 B1
(45) Date of Patent: Sep. 13, 2022

(54) IMPLANTABLE RESONATOR SYSTEM FOR DEEP-TISSUE EPR OXIMETRY WITH REDUCED NOISE

(71) Applicant: Clin-EPR LLC, Lyme, NH (US)

(72) Inventors: Harold M. Swartz, Lyme, NH (US); Ann Barry Flood, Lyme, NH (US); Wilson Schreiber, West Lebanon, NH (US)

(73) Assignee: CLIN-EPR LLC, Lyme, NH (US)

( * ) Notice: Subject to any disclaimer, the term of this patent is extended or adjusted under 35 U.S.C. 154(b) by 0 days.

(21) Appl. No.: 17/569,895

(22) Filed: Jan. 6, 2022

(51) Int. Cl.
  *A61B 5/055* (2006.01)
  *G01R 33/60* (2006.01)
  *A61B 5/145* (2006.01)

(52) U.S. Cl.
  CPC .......... *A61B 5/055* (2013.01); *A61B 5/14503* (2013.01); *A61B 5/14542* (2013.01); *G01R 33/60* (2013.01); *A61B 2562/16* (2013.01); *A61B 2562/225* (2013.01)

(58) Field of Classification Search
  CPC . A61B 5/055; A61B 5/14503; A61B 5/14542; A61B 2562/16; A61B 2562/225; G01R 33/60
  See application file for complete search history.

(56) References Cited

U.S. PATENT DOCUMENTS

| | | | | |
|---|---|---|---|---|
| 4,038,625 | A * | 7/1977 | Tompkins | H01F 38/14 336/83 |
| 2007/0018649 | A1* | 1/2007 | Prsha | G01V 3/088 324/326 |
| 2011/0130647 | A1* | 6/2011 | Swartz | G01R 33/286 324/307 |
| 2014/0163338 | A1* | 6/2014 | Roesicke | A61B 5/0031 600/309 |
| 2021/0408836 | A1* | 12/2021 | Smith | H02J 50/12 |

OTHER PUBLICATIONS

Caston et al. 2017 Cell Biochem. Biophys. 75:275-283 (Year: 2017).*
Schaner et al. 2021 Frontiers in Oncology 11 article 743256 18pages (Year: 2021).*
Salikhov et al. 2003 J. Magnetic Resonance 164:54-59 (Year: 2003).*
Chen et al. 2021 Applied Magnetic Resonance 52:1321-1342 (Year: 2021).*
Enomoto 2018 Magn. Reson. Med. 80:2288-2298 (Year: 2018).*

* cited by examiner

Primary Examiner — Colin T. Sakamoto
Assistant Examiner — Patrick M Mehl
(74) Attorney, Agent, or Firm — Polsinelli PC (57) ABSTRACT

The present invention relates to implantable resonator systems for deep-tissue EPR oximetry and methods of using thereof. The implantable resonator of the present disclosure includes a resonator with an implantable end, a transmission line, and an external end, wherein the external end further includes a coupling loop operably connected to a coupling device. The coupling device includes a clamping mechanism to ensure proper alignment of the coupling loop. The implantable resonator may be used to monitor a tissue.

18 Claims, 6 Drawing Sheets

IMPLANTABLE RESONATOR SYSTEM FOR DEEP-TISSUE EPR OXIMETRY WITH REDUCED NOISE

FIELD OF THE INVENTION

The present disclosure relates to an implantable resonator system for deep-tissue EPR oximetry. Therefore, the present disclosure relates to the fields of biomedical engineering and medicine.

BACKGROUND

Deep-tissue electron paramagnetic resonance (EPR) oximetry is an effective method for measuring oxygen levels in vivo.

Prior implantable resonator systems required the implantation of a loop below the surface of the tissue and generally utilized transcutaneous magnetic coupling to an externally placed loop that connects to a spectrometer. Several problems exist with this system. First, coupling the externally placed loop to the implanted loop is difficult due to the sensitivity of the system. Even the slightest misalignment between the two loops can greatly increase the amount of noise in the oximetry measurements. A lot of time is therefore used simply to ensure that the loop is properly aligned. Second, the motion of the subject can perturb the relationship between the two loops and cause misalignment. Third, the placement of the loop in superficial layers of tissue above the tissue to be measured compromises the integrity of the surface area above the tissue to be measured.

What is needed is an implantable resonator system that overcomes these problems and provides clearer deep-tissue EPR oximetry measurements.

SUMMARY OF THE INVENTION

Provided herein is a resonator system for EPR oximetry. The system includes a resonator having an implantable end, a transmission line, and an external end, the implantable end comprising a plurality of sensing loops comprising a plurality of sensors and the external end comprising a coupling loop operably connected to the plurality of sensing loops via the transmission line. The system also includes a coupling device. The coupling device includes a resonator loop operably connected to a spectrometer and operable to inductively connect to the coupling loop, and a clamping mechanism operable to couple the coupling loop to the resonator loop. The implantable end of the resonator is suitable for implantation within a tissue of a subject and the external end of the resonator is located externally from the subject. The coupling device may further include one or more alignment guides to align the coupling loop and the resonator loop parallel to each other. The system may further include a sleeve surrounding the implantable end of the resonator. In some aspects, the sleeve may include a biocompatible material. In some embodiments, the subject may be a human. The clamping mechanism may be operable to prevent misalignment of the resonator loop and the coupling loop. The coupling device may further include a feedback mechanism operable to indicate when the clamping mechanism is closed and the coupling loop is aligned with the resonator loop.

Further provided herein is a method of monitoring the oxygen in a tissue. The method includes providing a system of the present disclosure, implanting the plurality of sensing loops of the resonator in the tissue, and coupling the coupling loop to the resonator loop via the clamping mechanism of the coupling device. The method may further include measuring oxygenation of the tissue using electron paramagnetic resonance oximetry. The method may further include decoupling the coupling loop of the resonator from the coupling device. In some embodiments, the tissue may be a tumor, such as a cancerous tumor. In some examples, the tumor may include brain cancer, head and neck cancer, and cervical cancer. In some embodiments, the tissue may be monitored during a course of treatment. In some examples, the treatment may include radiation therapy, chemotherapy, immunotherapy, or combinations thereof. The method may further include removing the resonator from the tissue after completion of the course of treatment. In some embodiments, the system may produce reduced noise as compared to a system wherein the coupling loop is subcutaneously implanted in the subject. In examples, the system produces essentially no noise. In some additional examples, the system produces no noise.

BRIEF DESCRIPTION OF THE FIGURES

FIGS. 4A-4C show an exemplary resonator of the present disclosure.

DETAILED DESCRIPTION

Before the present invention is disclosed and described, it is to be understood that this invention is not limited to the particular methods, compositions, or materials disclosed herein, but is extended to equivalents thereof as would be recognized by those ordinarily skilled in the relevant arts. It should also be understood that terminology employed herein is used for the purpose of describing particular embodiments only and is not intended to be limiting.

Concentrations, amounts, and other numerical data may be expressed or presented herein in a range format. It is to be understood that such a range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 2 to about 50" should be interpreted to include not only the explicitly recited values of 2 to 50, but also include all individual values and sub-ranges within the indicated range. Thus, included in this numerical range are individual values such as 2, 2.4, 3, 3.7, 4, 5.5, 10, 10.1, 14, 15, 15.98, 20, 20.13, 23, 25.06, 30, 35.1, 38.0, 40, 44, 44.6, 45, 48, and sub-ranges such as from 1-3, from 2-4, from 5-10, from 5-20, from 5-25, from 5-30, from 5-35, from 5-40, from 5-50, from 2-10, from 2-20, from 2-30, from 2-40, from 2-50, etc. This same principle applies to ranges reciting only one numerical value as a minimum or a maximum. Furthermore, such an interpretation should apply regardless of the breadth of the range or the characteristics being described.

As used herein, the term "about" is used to provide flexibility to a numerical range endpoint by providing that a given value may be "a little above" or "a little below" the endpoint. For example, the endpoint may be within 10%, 8%, 5%, 3%, 2%, or 1% of the listed value. Further, for the sake of convenience and brevity, a numerical range of "about 50 mg/mL to about 80 mg/mL" should also be understood to provide support for the range of "50 mg/mL to 80 mg/m L." The endpoint may also be based on the variability allowed by an appropriate regulatory body, such as the FDA, USP, etc.

In this disclosure, "comprises," "comprising," "containing," and "having" and the like can have the meaning ascribed to them in U.S. Patent Law and may mean "includes," "including," and the like, and are generally interpreted to be open ended terms. The terms "consisting of" or "consists of" are closed terms, and include only the components, structures, steps, or the like specifically listed in conjunction with such terms, as well as that which is in accordance with U.S. Patent law. "Consisting essentially of" or "consists essentially of" have the meaning generally ascribed to them by U.S. Patent law. In particular, such terms are generally closed terms, with the exception of allowing inclusion of additional items, materials, components, steps, or elements, that do not materially affect the basic and novel characteristics or function of the item(s) used in connection therewith. For example, trace elements present in a composition, but not affecting the composition's nature or characteristics would be permissible if present under the "consisting essentially of" language, even though not expressly recited in a list of items following such terminology. In this specification when using an open ended term, like "comprising" or "including," it is understood that direct support should be afforded also to "consisting essentially of" language as well as "consisting of" language as if stated explicitly and vice versa.

As used herein, the phrase "essentially no noise" refers to a condition wherein the signal to noise ratio is 20/1 or greater.

As used herein, the term "subject" refers to a mammal. Examples of subjects include humans, horses, pigs, cattle, dogs, cats, rabbits, and aquatic mammals. In one aspect the subject may be human.

As used herein, the term "tissue" may refer to connective tissue (e.g., bone, blood, and lymph tissue), epithelial tissue (e.g., skin), muscle tissue (e.g., striated muscle and smooth muscle), and nervous tissue (e.g., neurons). In some embodiments, the tissue may be a tumor. In some aspects, the tumor may be cancerous; for example, the tumor may be brain cancer, head and neck cancer, cervical cancer, or other types of cancer.

I. Resonator System

As described above, fully implanted resonator systems are susceptible to movement of the subject, which impacts the signal received from the coupling loop of the resonator. The resonator system of the present disclosure provides marked improvement over the fully implanted resonator systems by having a portion of the resonator operable to be located externally from the subject via a flexible transmission line. It was surprising that a resonator could be configured to have both an implantable end that allows for monitoring over a period of time and an external end that allows for a properly aligned connection to a coupling device, resulting in essentially no noise in the signal received from the coupling loop.

Described herein is a resonator system for EPR oximetry that includes a resonator having an implantable end, a transmission line, and an external end. The implantable end of the resonator includes a plurality of sensing loops which include a plurality of sensors. The external end of the resonator includes a coupling loop. The coupling loop is operably connected to the plurality of sensing loops via the transmission line. The coupling loop operably connects to a coupling device. The coupling device includes a resonator loop and a clamping mechanism. The resonator loop is operably connected to a spectrometer and is operable to inductively connect to the coupling loop. The clamping mechanism is operable to couple the coupling loop to the resonator loop. The implantable end of the resonator is suitable for implantation within a tissue of a subject and the external end is located externally from the subject.

The resonator system includes a resonator. The resonator has an implantable end that is operable to be implanted in the tissue of a patient. The implantable end is operably connected to a transmission line.

Figure 1:
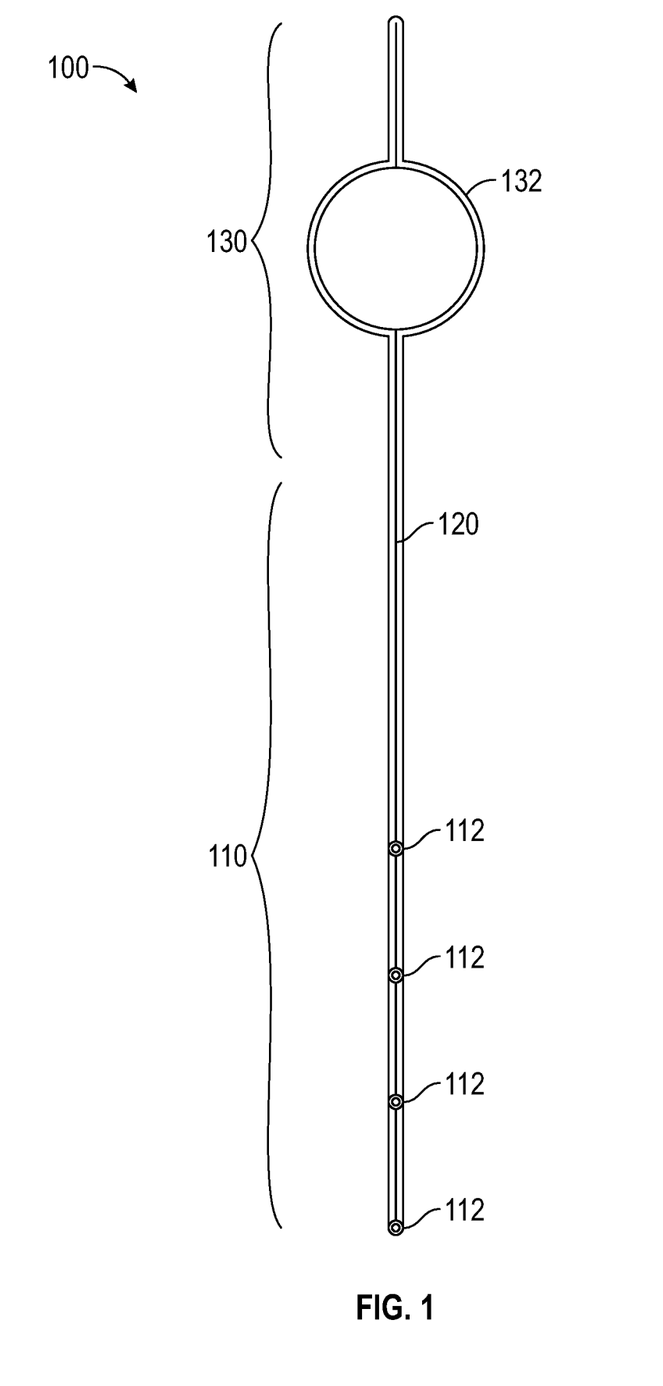
FIG. 1 shows a top-down view of an exemplary resonator of the present disclosure including the implantable end and the coupling loop.

Referring now to FIG. 1, an exemplary resonator 100 of the present disclosure includes an implantable end 110, a transmission line 120, and an external end 130. The implantable end 110 includes the transmission line 120 and a plurality of sensor loops 112. The external end 130 includes the transmission line 120 and a coupling loop 132. In this embodiment, the transmission line 120 is continuous with the coupling loop 132 and the plurality of sensor loops 112.

Figure 2:
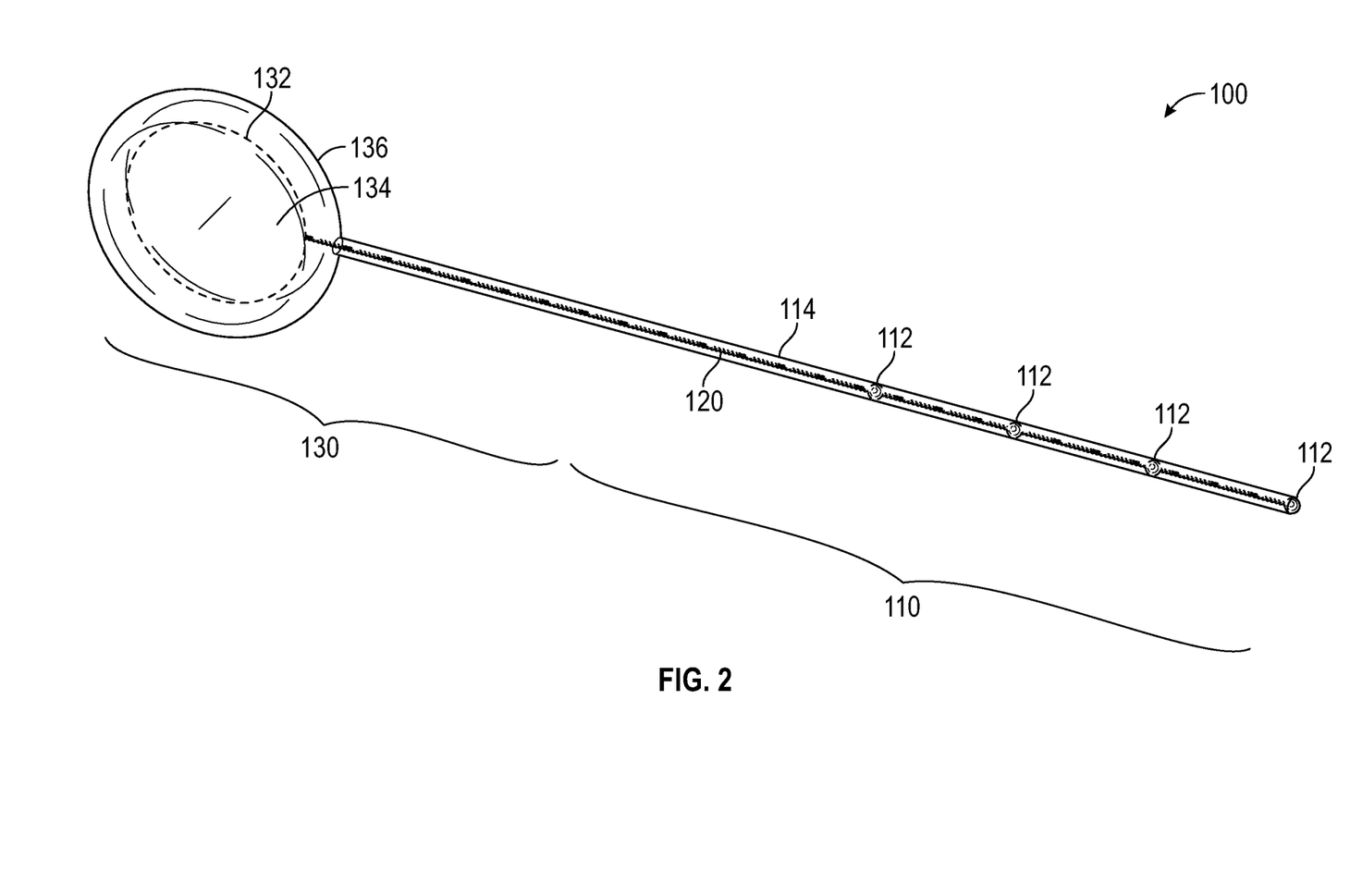
FIG. 2 shows a perspective view of an exemplary resonator of the present disclosure, including the implantable end and the coupling loop.

Referring now to FIG. 2, another exemplary resonator 100 of the present disclosure includes an implantable end 110, a transmission line 120, and an external end 130. The implantable end 110 includes polytetrafluoroethylene (PTFE) tubing 114 surrounding the plurality of sensor loops 112 and the transmission line 120. The external end 130 includes a coupling loop 132 and an insert 134 to maintain the disc shape of the coupling loop. The coupling loop 132 also includes an elastomer coating 136.

The implantable end 110 includes a plurality of sensor loops 112. Each of the plurality of sensor loops 112 includes a plurality of sensors. The sensor loops 112 are located at the distal portion of the implantable end 110. Each sensor loop 112 may be nominally about 0.7 mm in diameter. The plurality of sensors each includes one or more oxygen sensing materials embedded in an oxygen-permeable silicone elastomer, such as polydimethylsiloxane (PDMS). In some embodiments, the one or more oxygen sensing materials includes lithium phthalocyanine (LiPc) or lithium octa-n-butoxynaphthalocyanine (LiNc-BuO). In some embodiments, uncured LiNc-BuO crystals embedded in PDMS are inserted into each sensing loop 112 before curing. The number of sensor loops 112 in the system may be 1, 2, 3, 4, 5, 6, 7, 8 or more sensor loops 112. In some aspects, each of the plurality of sensor loops 112 may be separated by a predetermined distance measured from midpoint to midpoint to characterize heterogeneity and to facilitate signal detection. The predetermined distance may be determined based on the detection frequency of the resonator and the oxygen diffusion axially along the elastomer. In some embodiments, the predetermined distance may be about 5 mm to about 10 mm; for example, the predetermined distance may be about 5 mm, 6 mm, 7 mm, 8 mm, 9 mm, or about 10 mm. In some examples, the connection frequency may be about 1.15 GHz. In some embodiments, the connection to each of the plurality of sensor loops 112 may be flexible such that moderate physiological motion of the patient will not result in motion of the coupling loop.

The transmission line 120 includes a twisted pair of wires. The transmission line 120 is operably connected to each of the plurality of sensor loops 112 and to the coupling loop 132. The transmission line 120 is formed by an insulated conductive wire operable to transmit radio frequency (RF) energy from the coupling loop 132 to the plurality of sensor loops 112. In some embodiments, conductive wire may be a copper wire or, more preferably, a nickel-cobalt-chromium-molybdenum alloy. In an exemplary embodiment, the transmission line 120 is a twisted pair of MP35N wire having an average diameter of 0.004 inches. The transmission line 120 is flexible in order to conform to different contours and shapes of tissues, to respond to the subject's physiological movement without dislodging the plurality of sensing loops, and to prevent motion of the coupling loop. Physiological movement may include voluntary movement by the subject (e.g., movement of the limbs) or involuntary movement (e.g., expansion of lungs from respiration and heartbeat). In some embodiments, the transmission line may be continuous to form the coupling loop and the plurality of sensing loops.

The length of the implantable end 110 of the resonator system may vary to access various tissues within a subject. In some embodiments, the length of the implantable end 110 of the system may be about 1 cm to about 25 cm. In some aspects, the length of the implantable end 110 of the system may be about 1 cm to about 5 cm, about 5 cm to about 10 cm, about 10 cm to about 15 cm, about 15 cm to about 20 cm, or about 20 cm to about 25 cm. In some additional aspects, the length of the implantable end 110 of the system may be about 1 cm to about 10 cm, about 1 cm to about 15 cm, about 1 cm to about 20 cm, about 1 cm to about 25 cm, about 5 cm to about 25 cm, about 10 cm to about 25 cm, about 15 cm to about 25 cm, or about 15 cm to about 25 cm. In still further aspects, the length of the implantable end 110 may be about 1 cm, 5 cm, 10 cm, 15 cm, 20 cm, or about 25 cm.

In some embodiments, the resonator 100 may be surrounded by a very thin layer of an elastomer 114, such as polydimethylsiloxane (PDMS), to minimize tissue adherence and to secure the plurality of sensors from dislodgement. In some embodiments, the resonator 100 may be dip-coated in the elastomer 114 or the transmission line 120 and the plurality of sensor loops 112 may be inserted into an elastomer tube. In some aspects, the elastomer tube 114 may have an inner diameter of about 1.02 mm and a wall thickness of about 0.038 mm. In preferred embodiments, the elastomer does not have an EPR signal.

The external end 130 of the resonator system is located externally from the subject. The external end 130 of the resonator system includes a portion of the transmission line 120 and a coupling loop 132. The coupling loop may include a conductive wire operable to transmit RF energy. The coupling loop 132 is operably connected to the transmission line 120. In some embodiments, the wire forming the coupling loop 132 may be continuous with the transmission line 120. The coupling loop 132 may be operable to inductively connect to the resonator loop 142. In some embodiments, the coupling loop 132 includes an insert 134 to maintain the disc shape of the coupling loop 132. In some aspects, the insert 134 may be flexible to respond to mechanical stress. In some examples, the insert 134 may comprise a washer made of PTFE or PDMS. In some embodiments, the connection between the transmission line 120 and the coupling loop 132 is flexible such that physiological motion of the patient does not result in motion of the coupling loop 132.

Figure 3A:
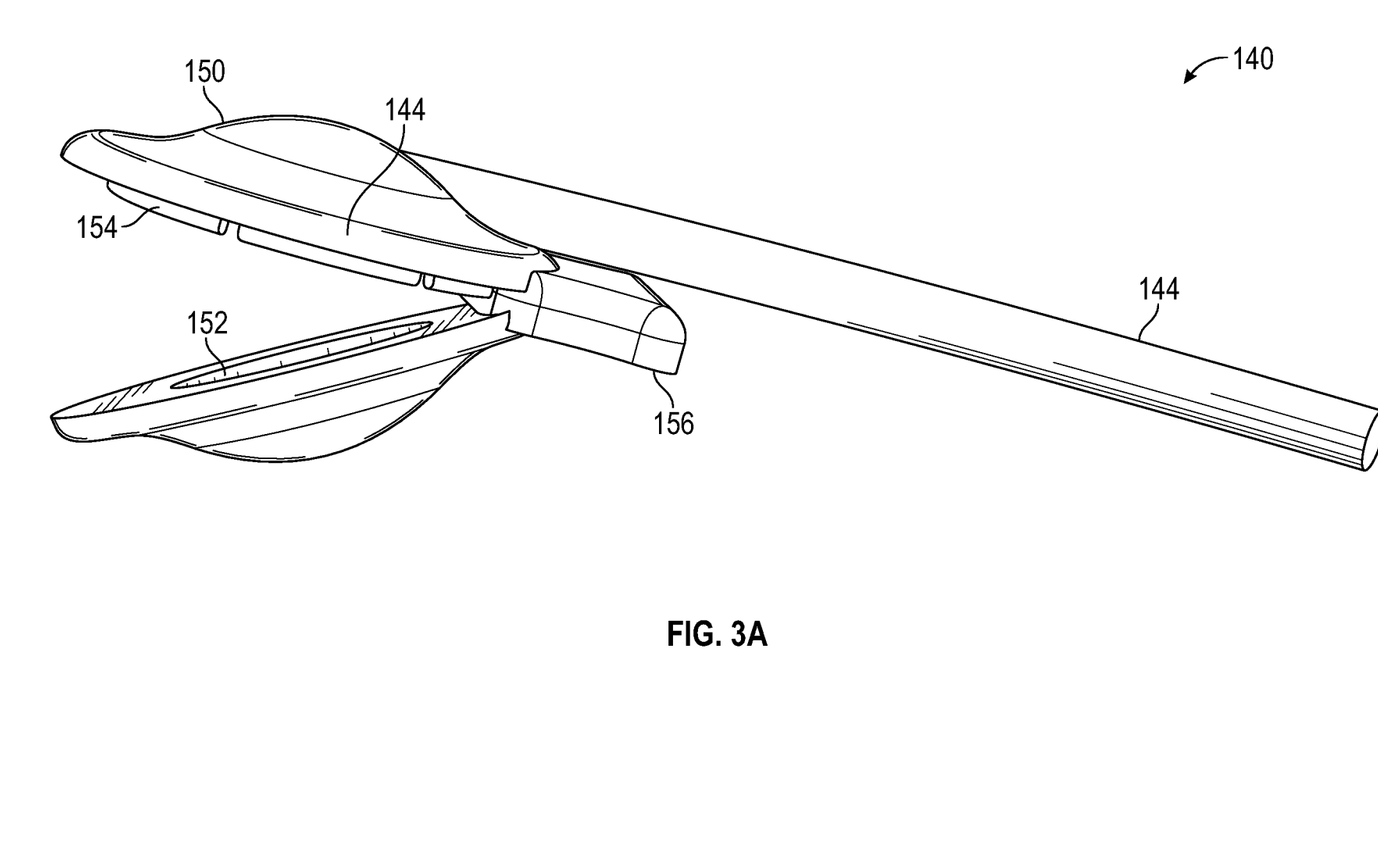
FIGS. 3A-3B show an exemplary coupling device of the present disclosure, with the clamping mechanism in an open position.
Figure 3B:
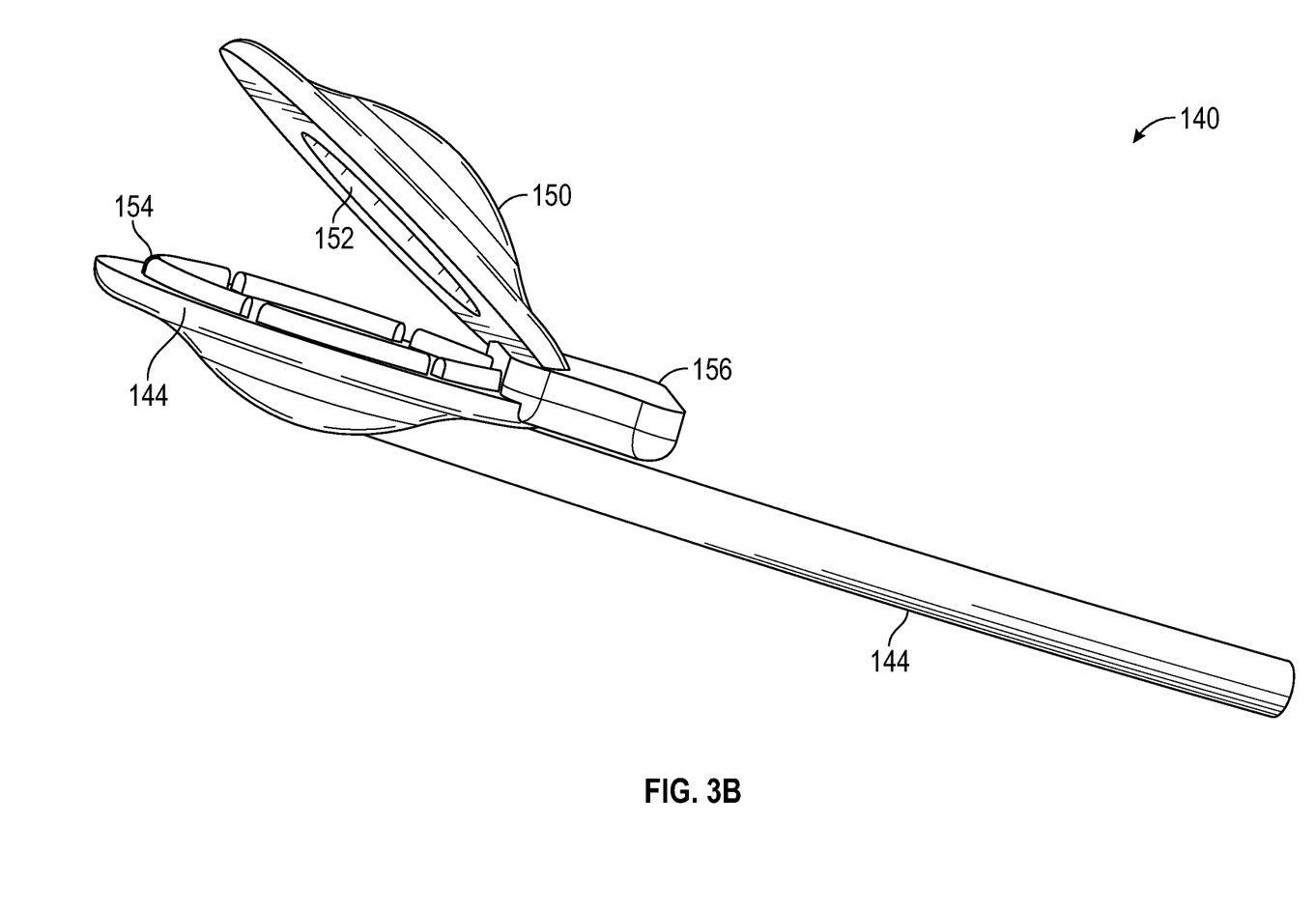

Referring now to FIGS. 3A-3B, an exemplary coupling device 140 of the present disclosure includes a clamping mechanism 150. The clamping mechanism 150 includes a circular pocket 152 to guide the alignment of the coupling loop 132, an alignment guide 154 to ensure the alignment of the coupling loop 132 and the resonator loop 142, and a RF cable 144 operable to connect the resonator loop 142 to an EPR spectrometer. The clamping mechanism 150 further includes a tab 156 operable to open the clamping mechanism when pressed by an operator. The tab 156 may be spring-loaded so that the clamping mechanism remains closed with no input from the operator.

The coupling loop 132 is operable to connect to a coupling device 140. The coupling device 140 includes a resonator loop 142. The resonator loop 142 is operably connected to an EPR spectrometer and is operable to inductively connect to the coupling loop 132. In some embodiments, the resonator loop 142 may have the same diameter as the coupling loop 132. In some additional embodiments, the resonator loop 142 may have a diameter slightly greater than the coupling loop 132. The resonator loop 142 is operable to inductively transmit RF signals to the coupling loop 132 and to inductively receive RF signals from the coupling loop 132.

In a particular embodiment, the resonator loop 142 comprises a PTFE flexible substrate with oxygen-free copper on either side (e.g. POLYFLON®). The profile of the wireless resonator loop 142 is etched into the copper cladding, and excess material is removed. This is then coated with a layer of silver with a thickness greater than or equal to the depth of the frequency of the EPR resonance condition. Oxygen-free copper and silver plating were utilized for these wireless sensors in order to eliminate magnetic components used near/on the resonant structure, and reduce the potential of unwanted spectral baseline and spectral distortions, as well as unwanted paramagnetic centers.

The coupling device 140 further includes a clamping mechanism 150 operable to couple the coupling loop 132 to the resonator loop 142. The coupling loop 132 and the resonator loop 142 must be precisely aligned parallel to each other to minimize noise created by physiological movement of the subject and/or misalignment of the coupling loop 132 and the resonator loop 142. The resonator loop 142 and the coupling loop 132 are aligned parallel to each other when the loops are placed in concentric alignment. The clamping mechanism 150 prevents movement of the coupling loop 132 and the resonator loop 142, thereby ensuring that the coupling loop 132 and the resonator loop 142 remain in proper alignment even when the subject moves or when the resonator is exposed to mechanical stress. In some embodiments, the clamping mechanism 150 may be spring-loaded to maintain the clamping mechanism 150 in a closed position without any input from an operator. In some aspects, the spring-loaded clamping mechanism 150 may have a tab 156 that an operator may press on to open the clamping mechanism to place or remove the coupling loop. In an exemplary embodiment, the clamping mechanism 150 includes a circular pocket 152 that aligns the coupling loop swiftly and ensures concentric placement of the coupling loop 132 and the resonator loop 142. In some aspects, the clamp may not close completely unless the coupling loop 132 and the resonator loop 142 are properly aligned.

In some embodiments, the coupling device 140 may further include a feedback mechanism. The feedback mechanism may be operable to detect and indicate whether the clamping mechanism 150 is in a closed position. In some aspects, the feedback mechanism may be operable to detect and indicate whether the resonator loop 142 and the coupling loop 132 are coupled and, preferably, whether the resonator loop 142 and the coupling loop 132 are properly aligned.

In some embodiments, the coupling device may further include one or more alignment guides 154 to align the coupling loop and the resonator loop parallel to each other. The alignment guides may include raised portions of wire or PTFE, markings on the coupling loop 132 that align with markings, divots, or guides on the clamping mechanism 150. In some embodiments, the alignment guides include a circular pocket 152 in the clamping mechanism 150. The circular pocket 152 is a recessed circular formation in the clamping mechanism 150 operable to receive the coupling loop 132. In some embodiments, the circular pocket 152 may be a negative of the external end 130 of the resonator. The circular pocket 152 ensures optimal concentric placement of the resonator loop 142 and the coupling loop 132 in a repeatable and simple fashion. In some embodiments, the alignment guides 154 may prevent the clamping mechanism 150 from closing if the alignment guides 154 are improperly positioned.

Figure 4A:
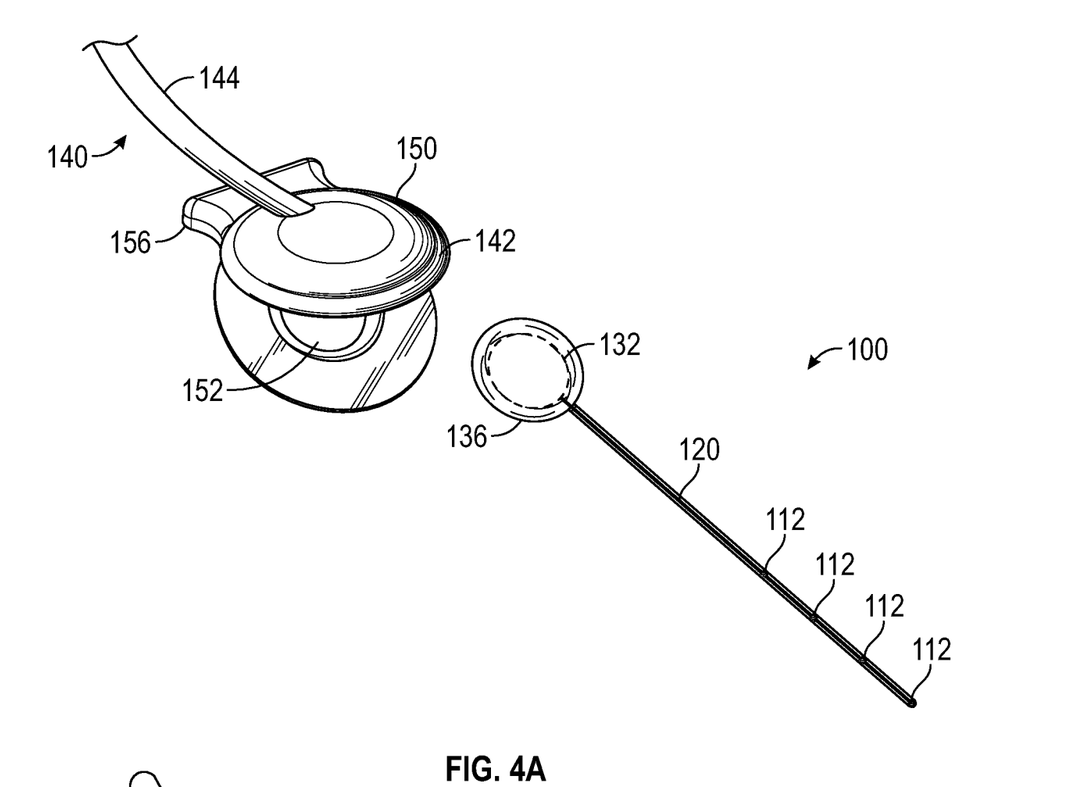
FIG. 4A shows the resonator with the coupling loop uncoupled to the resonator loop.
Figure 4B:
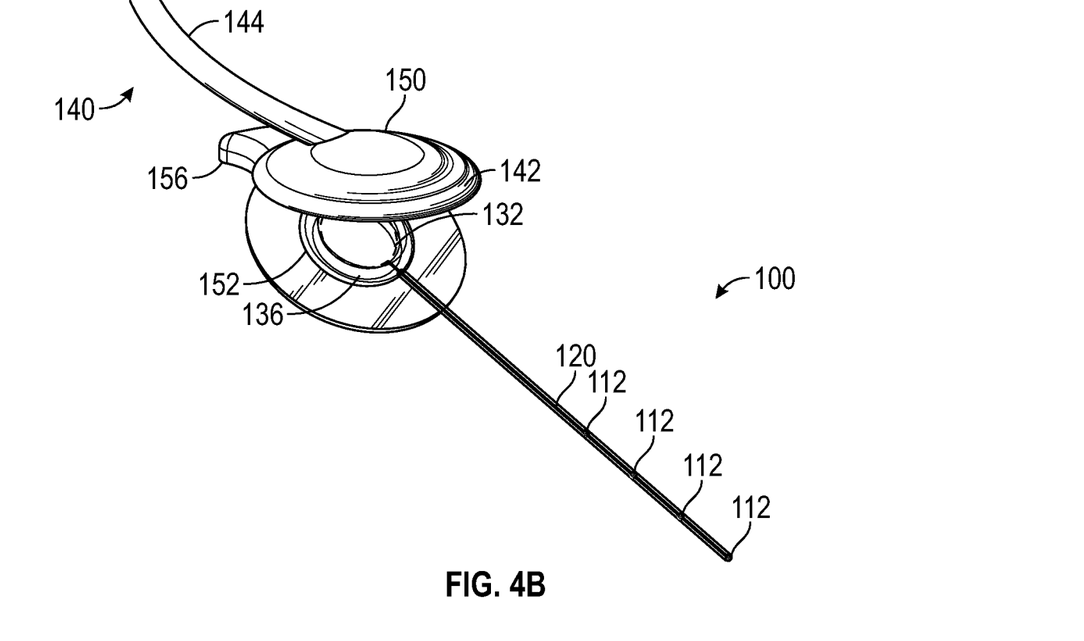
FIG. 4B shows the resonator with the coupling loop within circular pocket of the coupling device.
Figure 4C:
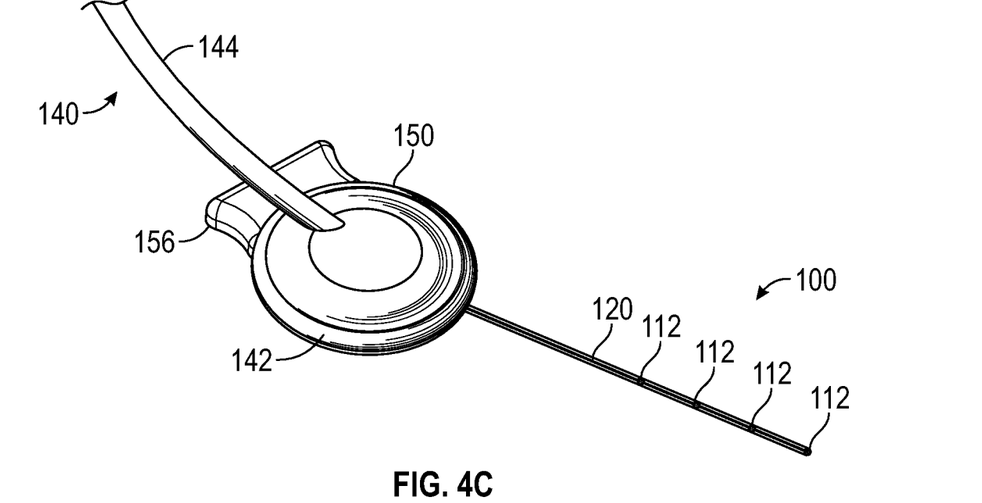
FIG. 4C shows the resonator with the coupling loop coupled to the resonator with the clamping mechanism in a closed position.

Referring now to FIGS. 4A-4C, an exemplary resonator system of the present disclosure includes a resonator 100 and a coupling device 140. The coupling loop 132 is placed within the circular pocket 152 of the clamping mechanism 150 to ensure that the coupling loop 132 and the resonator loop 142 are aligned parallel to each other. The clamping mechanism 150 is then closed.

Figure 5:
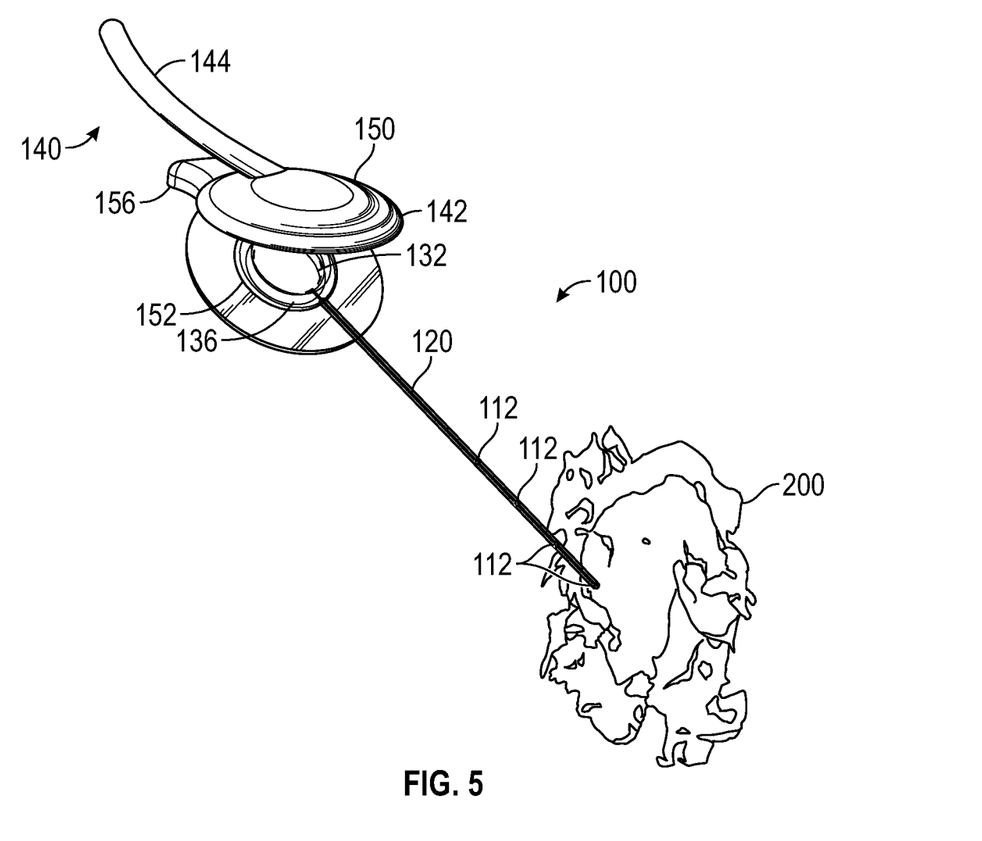
FIG. 5 shows an exemplary resonator of the present disclosure in relation to a tissue to be measured.

Referring now to FIG. 5, an exemplary resonator system of the present disclosure includes a resonator 100 and a coupling device 140. The implantable end 110 of the resonator 100 includes a plurality of sensor loops 112 implanted near the tissue 200 of a subject to be monitored.

In some embodiments, the resonator 100 may further comprise a sleeve. The system of the present disclosure may be used to measure oxygen levels in sensitive tissues, such as the cervix. Moreover, the system may be removed and/or readjusted. The sleeve may surround the implantable end 110 of the resonator 100 to protect surrounding tissues when the resonator is in place, when the resonator 100 is removed, and when the resonator 100 is readjusted. In some aspects, the sleeve may be the same length as the implantable end 110 of the resonator, or it may have a different length. In some aspects, the sleeve may be made of a biocompatible material. As used herein, a "biocompatible material" refers to any material which does not invoke a local or systemic adverse response by the subject, such as anaphylaxis, rash, swelling, inflammation, etc. In some embodiments, the biocompatible material may be PDMS, PTFE, polyvinylchloride, polyethylene, polyetheretherketone, polycarbonate, polysulfone, polypropylene, polyurethane, polyetherimide, or combinations thereof.

Fully implanted resonator systems are subject to noise in the signal from the coupled coupling loop 132 and resonator loop 142. The coupling loop 132 being external from the subject allows for the precise alignment of the resonator loop 142 and the coupling loop 132, which in turn allows the resonator system of the present disclosure to produce little to essentially no noise. The clamping mechanism 150 effectively eliminates most or all noise produced by the movement of the patient. Compared to a resonator system where the coupling loop 132 is implanted in the subject and the resonator loop 142 is external from the subject, the resonator system of the present disclosure produces much less noise because the coupling loop 132 is outside the body and is less susceptible to motion by physiological movements. The flexibility of the transmission line 120 also aids in preventing motion of the coupling loop 132. Moreover, the clamping mechanism 150 is able to maintain the proper alignment of the resonator loop 142 and the coupling loop 132 to improve the resulting signal. In some embodiments, the system has a signal to noise ratio greater than 1. In some additional embodiments, the system produces essentially no noise. In further embodiments, the system produces no physically or anatomically induced noise. In an exemplary embodiment, the system produces no noise.

In some embodiments, the resonator system of the present disclosure may be compatible with existing clinical EPR spectrometers.

In some embodiments, the resonator system may be reusable if sterilized.

In some embodiments, the resonator 100 may be compatible with different radiological techniques. Subjects may have to undergo radiology after the resonator is implanted. In some aspects, the resonator may be compatible with magnetic resonance imaging (MRI), computed tomography (CT), X-ray, positron emission tomography (PET), ultrasonography, fluoroscopy, nuclear medicine, mammography, and other radiological techniques.

II. Method of Monitoring a Tissue

Further described herein is a method of monitoring a tissue in a subject. The method includes providing a system described in Section I, implanting the plurality of sensing loops of the resonator in the tissue, and coupling the coupling loop to the resonator loop via the clamping mechanism of the coupling device. The method may further comprise measuring oxygenation of the tissue using electron paramagnetic oximetry.

Implanting the plurality of sensor loops may be accomplished through various methods. Those having skill in the art will appreciate that the method for implanting the plurality of sensor loops may be modified depending on many factors, including the type of tissue to be monitored, the anatomical location of the tissue, the health of the patient, etc., without departing from the scope of the invention. In one example, the implantable end may be placed in the cervix of a subject. The implantable end of the resonator may be contained within the vaginal canal similar to the end of an IUD. The flexible transmission line may then be operable extend out of the vaginal canal such that the coupling loop is outside the subject's body. In some examples, the coupling loop may remain in the vaginal canal when not in use and may be removed digitally when measurements need to be taken. Generally, after sterilizing the subject's skin an incision is made above the area where the plurality of sensor loops will be implanted. Bone or other tissue may be removed or retracted to provide access to the tissue to be monitored or to provide room for the plurality of sensor loops. For example, if the tissue to be monitored is located in the brain of a subject, a portion of the subject's skull and the dura may be removed during the implanting of the plurality of sensor loops. In some embodiments, the plurality of sensor loops may be implanted without the need for devices to guide the insertion, such as a catheter. In other embodiments, a catheter such as an angiocatheter or a peel-away catheter may be used to guide the implantation of the plurality of sensor loops. Once the plurality of sensor loops is placed, the incision is closed around the implantable end with the coupling loop external to the subject.

The method includes coupling the coupling loop to the resonator loop via the clamping mechanism. Coupling the coupling loop to the resonator loop via the clamping mechanism of the coupling device may be accomplished by opening the clamping mechanism, aligning the coupling loop with the resonator loop such that the two are aligned parallel to each other, and then closing the clamping mechanism. In some embodiments, the clamping mechanism may be spring-loaded such the clamping mechanism is kept closed when at rest. In some aspects, a spring-loaded clamping mechanism may include a tab that an operator presses with a finger or thumb to compress the spring and thus open the clamping mechanism. When the coupling loop is properly aligned, the operator releases the tab, closing the clamping mechanism. In some aspects, coupling the coupling loop to the resonator loop may further include aligning the coupling loop with the alignment guides on the coupling device.

In some embodiments, the method further includes decoupling the coupling device from the coupling loop of the resonator. Decoupling the coupling device from the coupling loop of the resonator may include opening the clamping mechanism and removing the coupling loop from the circular pocket.

In some embodiments, the tissue is monitored when the subject is undergoing a course of a treatment. The treatment may be selected from the group consisting of radiation therapy, chemotherapy, immunotherapy, or combinations thereof. In some aspects, the tissue may be monitored throughout the course of the treatment. In some additional aspects, the resonator may remain implanted throughout the entire course of the treatment.

In some embodiments, the resonator may remain implanted for about 1 week to about 12 weeks; for example, the resonator may remain implanted for about 1 week, 2 weeks, 3 weeks, 4 weeks, 5 weeks, 6 weeks, 7 weeks, 8 weeks, 9 weeks, 10 weeks, 11 weeks, or about 12 weeks. In some embodiments, the resonator may remain implanted for longer than about 12 weeks.

In some embodiments, the method may further include sterilizing the resonator system for reuse.

The above is only a preferred embodiment of the present invention, and does not limit the technical scope of the present invention. Therefore, any minor modifications, equivalent changes and modifications made to the above examples based on the technical essence of the present invention all fall within the scope of the technical solution of the present invention. Additionally, a number of well-known processes and elements have not been described in order to avoid unnecessarily obscuring the present disclosure. Accordingly, the above description should not be taken as limiting the scope of the disclosure.

Those skilled in the art will appreciate that the presently disclosed embodiments teach by way of example and not by limitation. Therefore, the matter contained in the above description or shown in the accompanying drawings should be interpreted as illustrative and not in a limiting sense. The following claims are intended to cover all generic and specific features described herein, as well as all statements of the scope of the present method and system, which, as a matter of language, might be said to fall therebetween.

What is claimed is:

1. A resonator system operable for use in electron paramagnetic resonance (EPR) oximetry, the system comprising:
   a resonator having an implantable end, a transmission line, and an external end, the implantable end comprising a plurality of sensing loops comprising a plurality of sensors and the external end comprising a coupling loop operably connected to the plurality of sensing loops via the transmission line; and
   a spring-loaded clamping mechanism operable to couple the coupling loop to a resonator loop, the clamping mechanism comprising:
      the resonator loop operably connected to a spectrometer and operable to inductively connect to the coupling loop;
      a recessed circular pocket operable to receive the coupling loop; and
      one or more raised alignment guides to align the coupling loop and the resonator loop parallel to each other,
   wherein the implantable end is suitable for implantation within a tissue of a subject and the external end is operable to be located externally from the subject, and
   wherein the system produces a signal to noise ratio of greater than 1 when the resonator loop is inductively connected to the coupling loop.

2. The system of claim 1, wherein the one or more raised alignment guides comprise wires and polytetrafluoroethylene (PTFE).

3. The system of claim 1, further comprising a sleeve surrounding the implantable end of the resonator.

4. The system of claim 1, wherein the spring-loaded clamping mechanism is configured to maintain a closed position without any input from an operator and comprises a tab operable to open the spring-loaded clamping mechanism.

5. The system of claim 1, wherein the implantable end has a length of 1 cm to 25 cm.

6. The system of claim 1, wherein the clamping mechanism is operable to prevent misalignment of the resonator loop and the coupling loop.

7. The system of claim 1, wherein the coupling device further comprises a feedback mechanism operable to indicate when the clamping mechanism is closed and the coupling loop is aligned with the resonator loop.

8. The system of claim 1, wherein the signal to noise ratio is 20 or greater.

9. A method of monitoring the oxygen in a tissue, the method comprising:
   providing a system of claim 1;
   implanting the plurality of sensing loops of the resonator in the tissue;
   coupling the coupling loop to the resonator loop via the clamping mechanism of the coupling device; and
   measuring oxygenation of the tissue using EPR oximetry.

10. The method of claim 9, further comprising decoupling the coupling loop of the resonator from the coupling device.

11. The method of claim 9, wherein the tissue is a tumor.

12. The method of claim 11, wherein the tumor is cancerous.

13. The method of claim 12, wherein the tumor is selected from the group consisting of brain cancer, head and neck cancer, and cervical cancer.

14. The method of claim 9, wherein the tissue is monitored during a course of treatment.

15. The method of claim 14, wherein the course of treatment is selected from the group consisting of radiation therapy, chemotherapy, immunotherapy, and combinations thereof.

16. The method of claim 14, further comprising removing the resonator from the tissue after completion of the course of treatment.

17. The method of claim 9, wherein the system produces reduced noise as compared to a system wherein the coupling loop is subcutaneously implanted in the subject.

18. The method of claim 9, wherein the signal to noise ratio is 20 or greater.

\* \* \* \* \*